United States Patent [19]
Hawkins

[11] 3,947,406
[45] Mar. 30, 1976

[54] PROCESS FOR THE PRODUCTION OF LACTAMS
[75] Inventor: Edwin George Edward Hawkins, Lower Kingswood, England
[73] Assignee: BP Chemicals (U.K.) Limited, England
[22] Filed: Sept. 12, 1967
[21] Appl. No.: 667,061

[30] Foreign Application Priority Data
Sept. 24, 1966 United Kingdom............... 42756/66
Oct. 20, 1966 United Kingdom ...............46971
Nov. 9, 1966 United Kingdom ...............50324
Mar. 3, 1967 United Kingdom ...............10071

[52] U.S. Cl.. 260/239.3 A; 260/293.86; 260/307 R; 260/404; 260/586 R
[51] Int. Cl............................................. C07d 53/06
[58] Field of Search...... 260/239.3, 239.3 A, 293.86

[56] References Cited
UNITED STATES PATENTS
3,000,879  9/1961  Phillips et al. ................... 260/239.3

Primary Examiner—Henry R. Jiles
Assistant Examiner—Robert T. Bond

[57] ABSTRACT
Compounds of formula

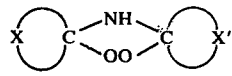

where X,X' are divalent aliphatic radicals which may be the same or different are heated to decompose them to lactams.

29 Claims, No Drawings

PROCESS FOR THE PRODUCTION OF LACTAMS

The present invention relates to a process for the production of lactams. Lactams may be polymerised to give useful polymers, e.g. caprolactam may be polymerised to give nylon-6.

According to the present invention the process for the production of lactams comprises heating in the liquid phase a compound of formula

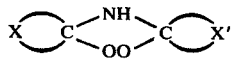   (IV)

where X, X' are divalent aliphatic radicals, which may be the same or different, to decompose it to lactam.

Compounds of formula (IV) comprise the class of compounds having the structural unit:

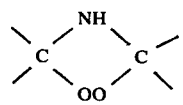   (I)

A wide range of atoms and groups may be attached to the free valencies in the structure (I)

Examples of groups which may be attached to the free valencies in structure (I) are hydrogen, alkyl and aryl groups. One, or both, of the carbon atoms in structure (I) may form part of a ring or rings into which they are bonded by their free valencies. Examples of suitable rings are those containing from 5 to 7 carbon atoms or more in the ring, and this ring may be joined to other rings.

It is found that compounds in which one or more of the free valencies are linked to hydrogen atoms may tend to be unstable and decompose. If therefore it is desired to store a compound of structure (I) for any length of time it should preferably not contain any hydrogen atoms bound to the free valencies.

Where neither of the carbon atoms in structure (I) forms part of a ring, it is preferred that at least one alkyl group be bonded to each carbon atom in the structure (I) the two remaining free valencies in structure (I) being satisfied by hydrogen, alkyl or aryl groups, to give compounds of formula

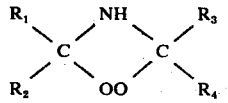   (II)

where $R_1$ and $R_3$ are alkyl and $R_2$ and $R_4$ are hydrogen, alkyl or aryl. The alkyl groups which may be the same or different are preferably lower alkyl groups e.g. having from 1 to 10 carbon atoms, in particular those having 1 to 5 carbon atoms.

Specific examples of compounds of formula (II) are:
2,2'-peroxy-diprop-2-ylamine

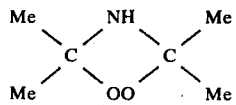

b.p. 40°–42°C at 12 m.m. Hg.

2,2'-peroxy-dibut-2-ylamine

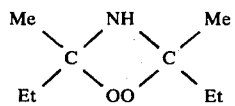

b.p. 66°–68°C at 12 m.m. Hg.
1,1'-peroxy-dibut-1-ylamine

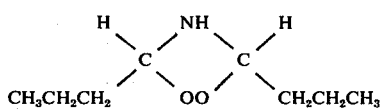

b.p. 50°C at 0.1 m.m. Hg.

As indicated above one of the carbon atoms in the structural unit (I) may form part of a ring into which it is bonded by the free valencies shown in the structure (I). Examples of such compounds are the compounds containing the structural unit

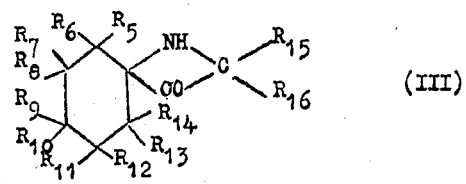   (III)

where $R_5$ to $R_{14}$ are hydrogen or alkyl groups, $R_{15}$ is alkyl and $R_{16}$ is hydrogen, alkyl or aryl. The alkyl group $R_{15}$, and $R_{16}$ when an alkyl group, are preferably lower alkyl groups for example those having less than 10, preferably less than 5 carbon atoms.

$R_5$ to $R_{14}$ may be hydrogen or alkyl and examples of suitable alkyl groups are the lower alkyl groups e.g. those having 1 to 5 carbon atoms in particular methyl, ethyl and propyl groups although longer alkyl chains may be also be used. Examples of compounds of formula (III) are those in which at least one of $R_5$ to $R_{14}$ is an alkyl group, in particular at least one of $R_7$ to $R_{12}$ is an alkyl group while $R_5$, $R_6$, $R_{13}$ and $R_{14}$ are hydrogen. An example of a particularly suitable pattern of substituents is that in which $R_7$ and $R_8$ are both methyl, while one of $R_{11}$ and $R_{12}$ is methyl the remaining $R_5$ to $R_{14}$ being hydrogen.

Both carbon atoms in the structural unit (I) may form part of rings into which they are bonded by the free valencies shown in the structure (I) and examples of such compounds are those of formula

   (IV)

where X,X' are divalent aliphatic radicals which may be the same or different.

In radicals X, X' the number of carbon atoms which are in the ring may for example vary from 4 to 11; i.e. the total number of carbon atoms in the ring may be between 5 and 12. Carbon atoms may be the only atoms in the ring. Examples of compounds of formula (IV) are those compounds where X is a radical having 4 to 6 carbon atoms in the ring. Examples of such compounds are:

(a) 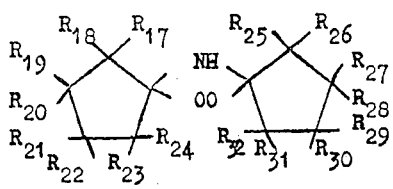 (V)

(b) 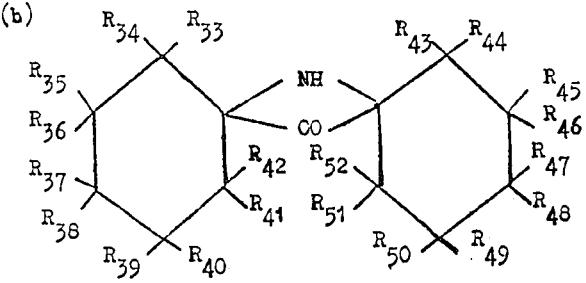 (VI)

and (c) 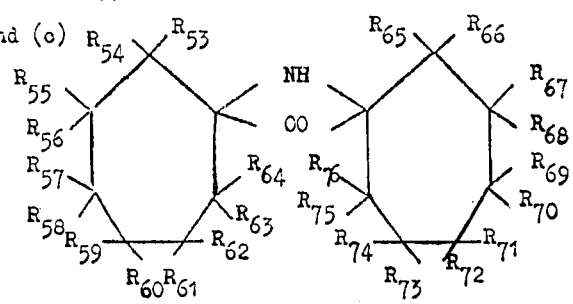 (VII)

where $R_{17}$ to $R_{76}$ are alkyl groups or hydrogen.

The preferred compounds are those in which $R_{17}$ to $R_{76}$ is hydrogen or lower alkyl, e.g. methyl, ethyl, propyl although the compounds may have longer chains.

Specific examples of compounds according to the present invention are:

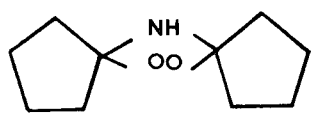

1,1'-peroxydicyolopentylamine which is a white solid with a melting point of 22°–23°C.

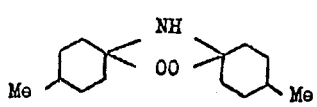

4,4'-dimethyl-1,1'-peroxydicyclohexylamine which is a white solid with melting point 119°–121°C.

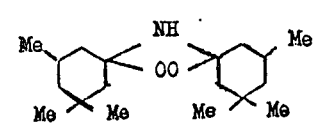

3,3,3',3',5,5'-hexamethyl-1,1'-peroxydicyclohexylamine which boils at 124°–126°C at a pressure of 0.4 mm.Hg.

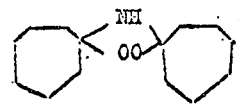

1,1'-peroxydicycloheptylamine which boils in the range 120°–130°C at a pressure of 0.8 mm.Hg.

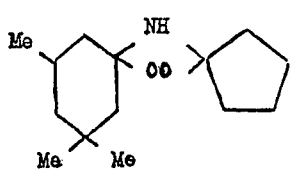

1,1'-peroxy-3,3,5-trimethylcyclohexyl cyclopentylamine which boils at 92°–96°C at 0.3 mm.Hg.

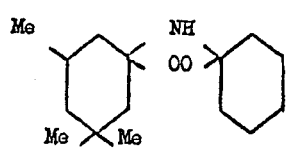

1,1'-peroxy-3,3,5-trimethylcyclohexyl cyclohexylamine

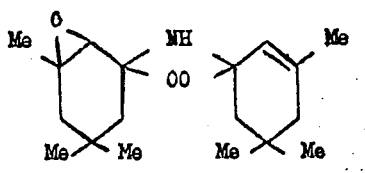

b.p. 136°–141°C at 0.3 mm.Hg.

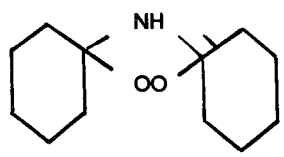

1,1'-peroxydicyclohexylamine which is a white solid insoluble in water but soluble in ethanol, which melts at 40°–41.5°C and distills at 94°–97°C at a pressure of 0.4 mm.Hg. and at 138°–140°C at a pressure of 12 mm.Hg.

Compounds having the essential skeletal structure (I) may be made by reacting together at least one compound having the essential skeletal structure:

 (IX)

with hydrogen peroxide and ammonia.

The free valencies of the carbon atom in the structure (IX) may be satisfied by any group which will be inert under the reaction conditions i.e. will not enter into reaction with ammonia or hydrogen peroxide.

The carbonyl compound may be acyclic or cyclio. Where the carbonyl compound is acyclic examples of suitable groups which may be bound to the free valencies are hydrogen and alkyl preferably lower alkyl. It is preferred that at least one alkyl group is bound to a free valency of the carbon atom of structure (IX) the other group being hydrogen or alkyl, to give compounds of formula

 (X)

where $R_{77}$ is alkyl and $R_{78}$ is hydrogen or alkyl. Preferably alkyl groups are bound to both free valencies. Specific examples of carbonyl compounds which may be used are acetone, ethyl methyl ketone, and n-butyraldehyde.

The compounds formed by reaction of a compound of formula (X) with hydrogen peroxide and ammonia are those of formula (II)

In place of acyclic carbonyl compounds, at least one compound of formula

 (XI)

where X is a divalent radical may be used. Carbon atoms may be the only atoms in the ring. The cyclic ketone may be for example a ketone with between 5 and 12 carbon atoms in the ring; would then have 4 – 11 carbon atoms forming part of the ring.

Examples of suitable ketones are those of formulae

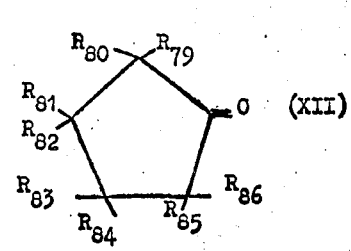

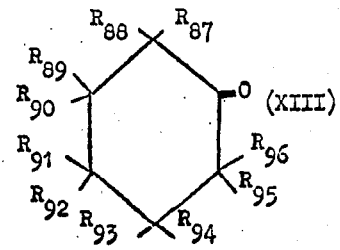

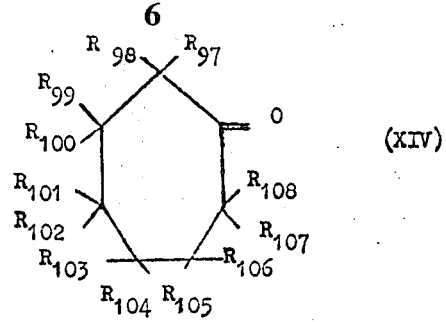 (XIV)

where $R_{79}$ to $R_{108}$ are alkyl groups or hydrogen.

The preferred compounds are those where $R_{79}$ to $R_{108}$ are hydrogen or lower alkyl e.g. methyl, ethyl, propyl, but compounds with longer alkyl chains can also be used. Examples of compounds of the above formulae which may be used are those in which not more than one alkyl group is joined to each carbon atom in the ring. Compounds in which two alkyl groups are joined to a single carbon atom may be used, however. When the ring is a 6 carbon atom ring, then any gem-dialkyl groups are preferably substituted in positions 3,4 or 5 on the ring.

Examples of ketones which may be used are cyclopentanone, 2-methylcyclohexanone, 3-methylcyclohexanone, 4-methylcyclohexanone, 3,3,5-trimethylcyclohexanone (dihydroisophorone), and cycloheptanone.

The compounds produced by reaction of a compound of formula (XI) with hydrogen peroxide and ammonia are those of formula (IV). Where only one compound of formula (XI) is used, and the radical X is inert under the reaction conditions the radicals X and X' in the compound of formula (IV) will be the same although the compound of formula (IV) may exist in a number of different stereoisomers.

It is possible that formation of compounds having the structural unit (I) from carbonyl compounds having the structure (IX) by reaction with ammonia and hydrogen peroxide proceeds by way of compounds containing the structural unit

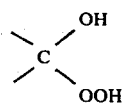 (XV)

and

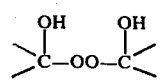 (XVI)

and where compounds of formula (XV) and (XVI) exist they may be reacted with ammonia to give compounds containing the structural unit (I). Thus the formation of compounds containing the structural unit (IV) by reaction of compounds of formula (XI), hydrogen peroxide and ammonia may proceed by way of compounds of formula

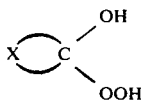
(XVII)

and

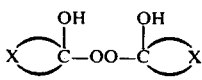
(XVIII)

where X is a divalent aliphatic radical, and where peroxides of the above formula can be formed e.g. by oxidation of cyclic alcohols with molecular oxygen or by reaction of cyclic ketones with hydrogen peroxide, these peroxides may be reacted with ammonia to give compounds of formula (IV)

Thus 1,1'-dihydroxydicyclohexyl peroxide

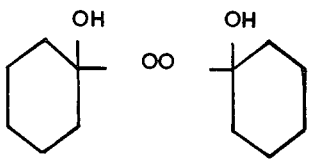

can be reacted with ammonia to give 1,1'-peroxydicyclohexylamine.

In the same way the formation of compounds of formula (II) from compounds of formula (X), hydrogen peroxide and ammonia may proceed by way of compounds of formula

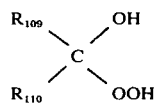
(XIX)

or

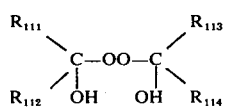
(XX)

where $R_{109}, R_{111}$ and $R_{113}$ have the same meaning as $R_{77}$ in formula (X) while $R_{110}, R_{112}$ and $R_{114}$ have the same meaning as $R_{78}$ in formula (X) and where these exist they may be reacted with ammonia to give compounds of formula (II).

It is possible that the formation of the compounds of formula (IV) from compounds of formula (XI), hydrogen peroxide and ammonia may proceed by way of an intermediate of formula

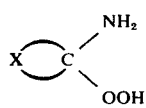
(XXI)

which then reacts further. Where compounds of formula (XXI) can be isolated they may be reacted with compounds (IX) to give compounds of formula (I). Thus compounds containing the structural unit (I) may be prepared by reacting a compound of formula

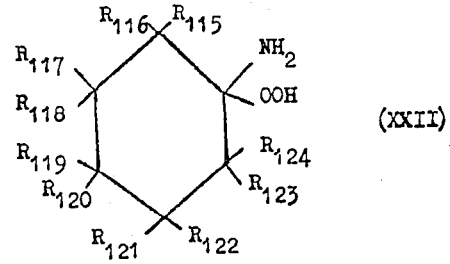
(XXII)

with a compound containing the structural unit $$O = C <$$ (IX)

$R_{115}$ to $R_{124}$ have the same meaning as $R_5$ to $R_{14}$ in structure (III) and the remarks made concerning $R_5$ to $R_{14}$ in connection with structure (III) apply also to $R_{115}$ to $R_{124}$ in the compound of formula (XXII). Before proceeding with the discussion of the reaction of (XXII) and (IX) it will be necessary to discuss the preparation of (XXII). Compounds of structure (XXII) may be prepared by reacting together a cyclic ketone of formula

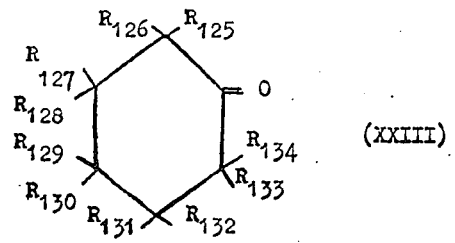
(XXIII)

with ammonia and hydrogen peroxide where $R_{125}$ to $R_{134}$ have the same meaning as $R_5$ to $R_{14}$ in formula (III) and the remarks made concerning $R_5$ to $R_{14}$ in connection with (III) apply also to $R_{125}$ to $R_{134}$ in (XXIII). A particularly preferred compound of formula (XXIII) is 3,3,5-trimethylcyclohexanone, as the compound of formula (XXII) namely 1-amino-3,3,5-trimethylcyclohexyl hydroperoxide is readily isolated from the reaction mixture before further reaction takes place.

A compound of formula (XXII) which may be produced by the process described above is 1-amino-3,3,5-trimethylcyclohexyl hydroperoxide. This compound whose structure was established by nuclear magnetic resonance and infra-red spectroscopy, and by elemental analysis is unstable if kept at temperatures much above 0°C and melts with decomposition at 67° – 67.5°C. The compound may be made by the process of the present invention using dihydroisophorone as the cyclic ketone

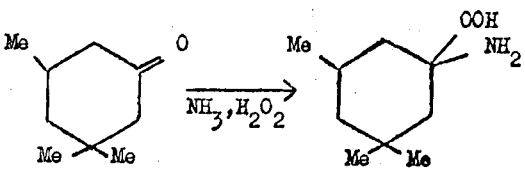

1-amino-4-methylcyclohexyl hydroperoxide may be made by using 4-methylcyclohexanone as starting material.

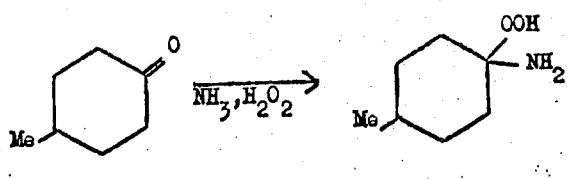

Other compounds of formula (XXII) are 1-aminocyclohexylperoxide

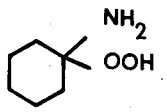

which has m.p. 57° – 58°C (rapid heating), 47°C with decomposition (slow Heating), and 1-aminocyclododecyl hydroperoxide which has m.p. of 72° – 73°C.

Having discussed the formation of the compounds of formula (XXII) I will return to the reaction of these compounds with compounds of formula (IX). The comments made concerning the groups which may be on the free valencies of the compound containing the structural unit (IX) in connection with the preparation of compounds containing the structural unit (I) apply also to the reaction of (XXII) and (IX). Thus compounds of formula (X) may be used, to give products of formula (II) while compounds of formula (XI) give products of formula (IV).

Examples of specific carbonyl compounds which may be used are formaldehyde, acetaldehyde, n-butyraldehyde, acetone, ethyl methyl ketone, diethylketone, acetophenone, cyclopentanone, cycloheptanone, and 3,5,5-trimethylcyclohexanone.

All the reactions described above can be carried out without a catalyst, although catalysts can be used, by bringing the reactants into contact. This may be done by mixing the reactants in the liquid phase. Where the reactants are all liquids or gases as may often be the case when carbonyl compounds of structure (IX), hydrogen peroxide and ammonia are being reacted together, simple mixing of the reactants may be sufficient. Where one of the reactants is a solid it may be dissolved in a solvent, which should preferably be miscible with the other constituents of the reaction mixture. Thus when reacting carbonyl compounds with hydrogen peroxide and ammonia the solvent used should be miscible, preferably completely, with hydrogen peroxide and water. Even if the reactants are all liquids or gases it may be desirable to add a solvent to ensure adequate contact between the reactants. Thus when reacting carbonyl compounds, hydrogen peroxide and ammonia together it may be desirable to add a liquid which is a solvent for the carbonyl compound and is miscible preferably completely with hydrogen peroxide and water. It may often be convenient to use a solvent in which the reactants are soluble and the desired reaction product insoluble so that the reaction product can be separated from the reaction mixture by filtration. This may be particularly useful when dealing with the less stable products, as the need to carry out distillations or solvent extractions which can cause considerable losses of product is thereby avoided. Examples of solvents which may be used are methanol, ethanol, light petroleum, ether, dioxan, dimethylformamide.

When bringing reactants into contact to carry out the reaction it is not essential that all the reactants should be entirely in the liquid phase and it may be desirable to mix the reactants together in the presence of a solvent for one of the reactants and the reaction product.

Where hydrogen peroxide is a reactant it will generally be in the form of an aqueous solution. The strength of this solution may vary between moderately wide limits. Examples of suitable hydrogen peroxide solutions are those containing between 5 and 100% by weight of the total solution of hydrogen peroxide. Thus commercially available solutions containing about 28–30% by weight of hydrogen peroxide are satisfactory. The reaction mixture may contain a hydrogen peroxide stabiliser e.g. sodium ethylene diamine tetraacetate (EDTA).

The concentration of hydrogen peroxide in the reaction mixture in which it is used will depend not only on the strength of the hydrogen peroxide solution added but on the quantities of other reactants and solvents present. The quantity of hydrogen peroxide in the reaction mixture may vary over a wide range. Examples of suitable concentrations of hydrogen peroxide in the reaction mixture are those in the range 5–40% by weight, particularly suitable concentrations being those in the range 10–20% by weight.

In the reaction of carbonyl compound (IX) with hydrogen peroxide and ammonia the molar ratio of ketone and hydrogen peroxide reacted together may vary over a moderately wide range for example between 4:1 and 0.5:1 but when preparing compounds having the structural unit (I) it is preferred to use at least two moles of ketone for one mole of hydrogen peroxide the stoichiometric ratio being 2:1. When it is desired to prepare compounds of formula (XXII) it is preferred to use a molar ratio of ketone to hydrogen peroxide of about 1:1, this being the stoichiometric ratio for the reaction.

Where ammonia is a reactant it may be fed into the reaction mixture in the form of a gas or as a solution in for example water. The concentration of the ammonia solution may vary over moderately wide limits and 0.880 ammonia i.e. an aqueous solution having a relative density of 0.880, is suitable. If desired the reaction may be started with the ammonia added to the other reactants as a solution and may be continued by passing gaseous ammonia into the reaction mixture. Where ammonia is a reactant it is preferred to use a slight excess over the stoichiometric quantity but the quantity of ammonia is not critical.

The temperatures at which the reactions described above may be carried out will depend upon the thermal stability of the reactants and products as the use of temperatures sufficiently high to decompose the reactants and products must be avoided.

When preparing compounds of structure (I) in which the free valencies of both carbon atoms do not bond the carbon atoms into a ring e.g. when preparing compounds of formulae: (II) or (III). Examples of temperatures which may be used are temperatures in the range −20°C to +20°C, in particular −10°C to +10°C. When reacting compounds of formula (XI) with hydrogen peroxide and ammonia or compounds of formula (XVII) or (XVIII) with ammonia it may be possible to use a somewhat wider range of temperatures, for example temperatures in the range −20°C to +60°C, preferably those in the range 0°C to 50°C. Temperatures of about 40°C are often particularly suitable. In the preparation of compounds of formula (XXII) and in the reaction of those compounds with compounds (IX) it is preferred to use temperatures in the range −20°C to +20°C, for example temperatures in the range −10°C to +10°C in particular temperatures below 0°C. The duration of the reaction when preparing compounds containing the structural unit (I) will depend upon the temperature and the particular reactants used and may vary over a wide range. The reaction may be complete in 2 to 3 hours but longer times may sometimes be desirable.

When preparing amino-hydroperoxides of formula (XXII) it may be necessary to control the reaction time carefully to prevent the compound (XXII), reacting further. The optimum time for this reaction can be determined by the man skilled in the art and may for example range from one-half to 7 hours. The pressure in the reactions described above may vary over a moderately wide range, atmospheric pressure or pressures close to atmospheric pressure generally being most convenient. When carrying out reaction in which ammonia is a reactant pressures below atmospheric pressure will cause a reduction in the ammonia concentration in the reaction system which may lead to reduced yields and it may be desirable to use pressures above atmospheric pressure to obtain a high concentration of ammonia.

The reactions described above can be carried out batchwise or continuously.

The peroxide (I) and (XXII) may be recovered in any suitable manner or may be used, without recovery, in further reactions. Where the reaction is carried out in aqueous solution the peroxide of formula (I) will generally separate out as a solid or in a liquid layer from the aqueous solution. Where the peroxide (I) is to be reacted further, this product rich in peroxide (I) can be separated from the reaction mixture and used without further purification. Alternatively the peroxide (I) may be extracted from the reaction using a suitable organic solvent e.g. chloroform, ether, light petroleum, benzene, or ethyl acetate. The peroxide (I) may then be separated from the extract by distillation, if necessary under reduced pressure, provided that the distillation temperature is not so high as to decompose the peroxide. Alternatively, it may be possible to precipitate the peroxide from the extract by addition of water. It may also be possible to obtain the solid crystalline peroxide directly by filtration from the reaction mixture.

The 1-amino-hydroperoxides (XXII) will often precipitate from the reaction mixture and can be separated by filtration from the reactants. Where other products are obtained which are insoluble in the reaction mixture it may often be possible to dissolve these other products with hydrophobic solvents e.g. light petroleum.

It should be noted that the compounds are not restricted to those made from carbonyl compounds (IX) carrying groups which are inert under the reaction conditions. The groups bonded to the free valencies shown in structure (I) may well differ from those found in the compounds from which the compound of structure (I) is prepared. Thus when ammonia and hydrogen peroxide are reacted together with a carbonyl compound which contains groups which react with ammonia and/or hydrogen peroxide it may often still be possible to obtain compounds containing the structural unit (I) but the groups bonded to the free valencies in the structure (I) will not necessarily then be the same as those bonded to the carbonyl group in the starting material.

The compounds (I) are also illustrated by the following Examples. The perchloric acid equivalents substances given in the examples were determined by titrating an anhydrous N/10 solution of perchloric acid in acetic acid with a solution in acetic acid of a weighed sample of the substance whose equivalent is being determined. The peroxide or active oxygen equivalents of substances given in the examples were determined by adding a saturated solution of potassium iodide (containing a quantity of potassium iodide in excess of that required to react with all the peroxide groups in the substance under investigation), to acetic acid to which a small quantity of sodium bicarbonate is added to generate carbon dioxide. A weighed sample of the substance under investigation is then added, the mixture heated on a boiling water bath for 5 minutes, and then cooled. A little water is then added and the mixture titrated with N/10 sodium thiosulphate solution.

EXAMPLE 1

Acetone (58 g.), 30% hydrogen peroxide (70 c.c.) and the sodium salt of E.D.T.A. (1.0 g.) were mixed and saturated with gaseous ammonia at about 0°C, and the solution stored overnight at 0°C. The solution was extracted with ether and the ethereal extract dried and evaporated. Distillation of the residue gave a fraction (21.1 g.), b.p. 55°/12 m.m., which on redistillation gave a product b.p. 40° – 42°C at 12 m.m.Hg. This product on analysis was shown on the basis of elemental analysis, nuclear magnetic resonance, and infra-red spectroscopy to be 2,2′-peroxy-diprop-2-ylamine

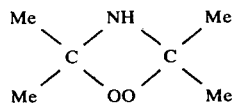

The peroxide equivalent was 135 and the perchloric acid equivalent was 147. The elemental analysis gave C, 55.05%; H, 10.1%; N, 10.2%.

EXAMPLE 2

Ethyl methyl ketone (72 g.), 30% hydrogen peroxide (70 c.c.), ammonium acetate (8 g.) and sodium salt of E.D.T.A. (1.- g.) were mixed and treated with gaseous ammonia as in Example 1. The solution was stored at 0°C overnight and then extracted with ether. Distillation of the ethereal extract gave a fraction (46.7 g.), b.p. 66°– 68° at 12 m.m.Hg. pressure. The peroxide equivalent was 157, the perchloric acid equivalent was 161 and the elemental analysis was C,59.4%; H,10.85%; N,8.4%.

This was identified as 2,2′-peroxy-dibut-2-ylamine

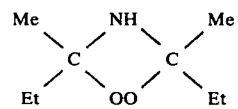

EXAMPLE 3

A mixture of n-butyraldehyde (72 g.), 30% hydrogen peroxide (70 c.c.), methanol (45 c.c.), ammonium acetate (8 g.) and sodium salt of E.D.T.A. (1 g.) was cooled to about 0°C and saturated with gaseous ammonia. The solution was stored at 0°C overnight and extracted with ether. The ethereal extract was evaporated to leave a residue (74.5 g.) having a peroxide equivalent of 171. A small portion of this residue was distilled to give a fraction b.p. 50°C at 0.1 m.m.Hg., with peroxide equivalent of 165 and a perchloric acid equivalent of 188, and elemental analysis C,60.5%; H,10.95% and N,8.9%.

This product was identified as 1,1'-peroxy-dibut-

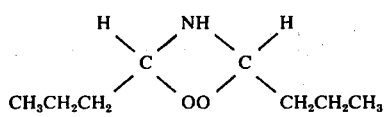

EXAMPLE 4

A mixture of isophorone (41.4 g.), 30% hydrogen peroxide (45.2 c.c.), methanol (350 c.c.), 0.880 ammonia (80 c.c.), and sodium salt of E.D.T.A. (1.0 g.) was cooled to temperatures at or below 0°C and saturated with gaseous ammonia, then stored at 0°C for several days. A solid (0.8 g.) was filtered off, rinsed with cold ethanol and refiltered, to give material with m.p. 74° – 81°, perchloric acid equivalent 1.79. Elemental analysis gave C, 56.2%; H, 9.2%; N, 7.1%. Spectroscopic evidence showed this to be the 1-amino-1-hydroperoxide of epoxyisophorone

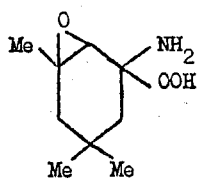

The filtrate was extracted with ether and the ethereal extract evaporated and distilled to give a fraction (27.7 g.) b.p. 54°C at 0.3 mm. Hg; consisting mainly of isophorone epoxide with some isophorone, and a fraction (3.4 g.) b.p. 136° – 141°C at 0.3 mm. Hg, with perchloric acid equivalent of 340 and active oxygen equivalent of 199. Elemental analysis gave C, 69.4%, H, 9.2%, N, 5.3%.

This peroxide

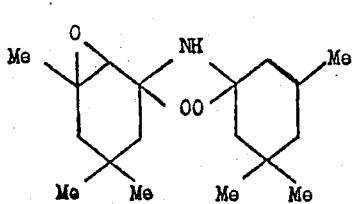

was of the type according to the present invention and this example illustrates the production of compounds according to the present invention from carbonyl compounds in which the groups bound to the carbonyl group are not inert.

EXAMPLE 5

1-Amino-3,3,5-trimethylcyclohexyl hydroperoxide (34.6 g.) was added with stirring to acetaldehyde (12 g.) in petrol (light petroleum spirit (b.p. 40° – 60°C))(60 c.c.) with the temperature kept at below 0°C. When the peroxide had dissolved, the aqueous layer was separated, and the organic phase treated with concentrated sulphuric acid (6 drops) and magnesium sulphate and left at room temperature. The solution was then filtered, washed with water, dried, and distilled. In addition to dihydro-isophorone a product (32.0 g.) was obtained which boiled at 70° – 78°C at 0.5 mm. Hg. pressure, and had a peroxide equivalent of 221. Elemental analysis gave C, 66.3%; H, 10.6%; N, 7.0%. This was identified as:

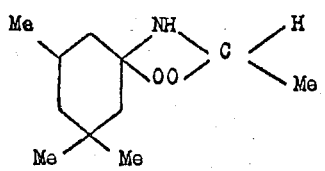

EXAMPLE 6

1-Amino-3,3,5-trimethylcyclohexyl hydroperoxide (17.3 g; 78% pure) was added with stirring to acetaldehyde (12 g.) in light petroleum (b.p. 40° – 60°C) 50 c.c.) with cooling to below 0°C. When the hydroperoxide had dissolved, the organic layer was separated, treated with solid magnesium sulphate and stored at 0°C overnight. The solution was then filtered, washed and distilled as in Example 1 and gave, in addition to dihydroisophorone, the same product (13.0 g.) as Example 1.

EXAMPLE 7

The process of Example 1 was repeated but using 17.3 g. of 78% pure 1-amino-3,3,5-trimethylcyclohexyl hydroperoxide, 30 c.c. of light petroleum and 3 drops of sulpuric acid. The reaction mixture was allowed to stand at 0°C for 4 hours and then worked up as in Example 1 to give the same peroxide product as in Example 1 (15.4 g.).

This product on redistillation had a b.p. of 68° – 74°C at 0.5 mm.Hg. pressure. On analysis the redistilled product gave C, 66.3%; H,10.6%; N, 7.0%. The calculated values were C, 66.3%; H, 10.55%; N, 7.0%.

EXAMPLE 8

Butyraldehyde (14.4 g.) was mixed with petrol (b.p. 40° – 60°) (50 c.c.) and to the stirred solution at <0° was added 1-amino-3,3,5-trimethylcyclohexyl hydroperoxide (17.3 g.; 89% pure). The peroxide dissolved within a few minutes. To the solution were added magnesium sulphate and concentrated sulphuric acid (6 drops) and the mixture stored at 0° overnight. The solution was filtered, the filtrate washed with water, dried and distilled to give unreacted butyraldehyde, dihydroisophorone and a product (11.1 g.), b.p. 85° – 110°/1.0mm. with a peroxide equivalent of 231, and a perchloric equivalent of 233. The elemental analysis gave C, 68.6%; H, 11.:5%; N, 6.6%. The product was identified as:

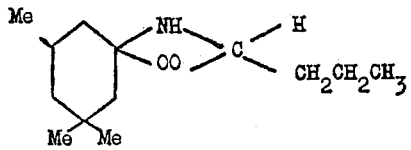

EXAMPLE 9

Butyraldehyde (28.8 g.) in petrol (100 c.c.) was cooled to below 0° and with stirring treated with 1-amino-1-hydroperoxy-3,3,5-trimethylcyclohexane (33 g.; 93% pure). When the solid had dissolved the aqueous phase was removed and the petrol solution dried with magnesium sulphate overnight at 0°. The working up as in Example 4 gave butyraldehyde, dihydroisophorone and the same peroxide (33.0 g.) b.p. 96° – 98°/0.6 mm. as in Example 4.

EXAMPLE 10

Formaldehyde (17.2 g. of 35% aqueous solution) was stirred in ether (50 c.c.), together with sodium bicarbonate (2 g.) at below 0° (and 1-amino-3,3,5-trimethylcyclohexyl hydroperoxide (16.5 g.; 96% pure) added. When the solid had dissolved the aqueous layer was removed and magnesium sulphate added to the ethereal solution, which was stored at 0°C for 2 hours. The solution was filtered and the filtrate evaporated at 15 mm.; the residue was then heated to 54°C at 0.6 mm. Hg. pressure and the fresh residue (9.0 g.), with a peroxide equivalent of 312, was shown, by mass spectrometry, to contain the peroxide

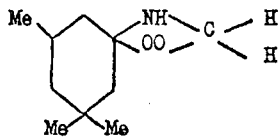

together with higher moleculer weight material.

EXAMPLE 11

Acetone (11.6 g.) in ethanol (50 c.c.) was stirred at below 0°C and 1-amino-3,3,5-trimethylcyclohexyl hydroperoxide (17.3 g.; 80% pure) added. After stirring for ca. 1 hour the solid had dissolved. To the solution was added magnesium sulphate and it was stored at 0° overnight. Filtration and distillation gave acetone and dihydroisophorone (probably containing some symmetrical amino-peroxide

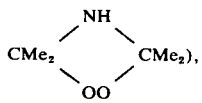

and a product (2.2 g.), b.p. 75° – 78°/1.0 mm, had a peroxide equivalent 239.4 and gave N, 6.3% an elemental analysis.

This was identified as the peroxide

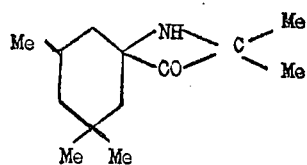

Redistillation of the peroxide gave a sample of the peroxide with a peroxide equivalent of 222, perchloric acid equivalent 235.

EXAMPLE 12

To a stirred mixture of ethyl methyl ketone (57.6 g.) and ethanol (200 cc.), containing ammonium acetate (6.4 g.) and kept at or below 0°C was added 1-amino-3,3,5-trimethylcyclohexyl hydroperoxide (69.2 g; pure). After the solid had dissolved the solution was stored at 0°C overnight. The product was worked up as in the previous Examples to give, on distillation, unreacted ethyl methyl ketone, a fraction (59.4 g.), b.p. 40° – 50°/0.4 mm, having a peroxide equivalent of 303 and shown by mass spectroscopy to be a mixture of dihydroisophorone and the symmetrical peroxide

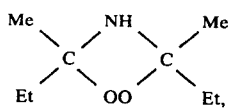

and a fraction (22 g.), b.p. 74° – 78°/0.4 mm., with a perchloric acid equivalent of 231 and perchloric acid equivalent of 227. The elemental analysis gave C, 69.0%; H, 11.2%; N, 5.8% which was identified as being the peroxide

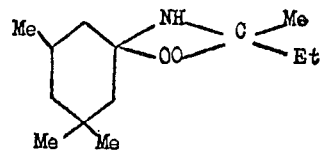

EXAMPLE 13

To a stirred solution of acetophenone (24.3 g.) in ethanol (50 c.c.) containing ammonium acetate (1.6 g.) and kept at or below 0°C, was added 1-amino-3,3,5-trimethylcyclohexyl hydroperoxide (17.3 g.; pure). The solution was kept at 0°C overnight and then worked up as in the previous Examples to give unreacted acetophenone and dihydroisophorone, and a fraction (4.8 g.), b.p. 126° – 130°/0.5 mm. with a peroxide equivalent of 407, shown by mass spectroscopy to contain the peroxide

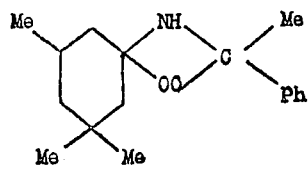

together with some of the symmetrical peroxide

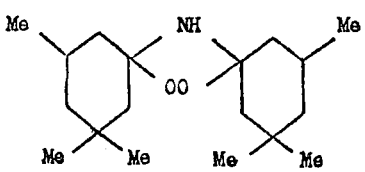

EXAMPLE 14

To a stirred mixture of cyclopentanone (33.8 g.) and ethanol (100 c.c.) containing ammonium acetate (3.2 g.) and kept at or below 0°, was added 1-amino-3,3,5-trimethylcyclohexyl hydroperoxide (44.6 g., 68% pure). After storing at 0°C overnight the reaction mixture was worked up as in the previous Examples to give unreacted cyclopentanone and dihydroisophorone together with a fraction (20.0 g.) b.p. 82° – 86°/0.5 mm. This last fraction was redistilled to give: material b.p. 74° – 76°C/0.3 mm.Hg., peroxide equivalent 202, shown by mass spectroscopy to be a mixture of the peroxide

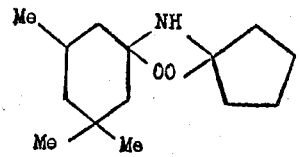

with the symmetrical peroxide

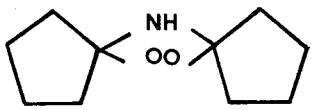

and material b.p. 92° – 96°/0.3 mm, peroxide equivalent 232, shown to be the unsymmetrical component of the mixture referred to above. On analysis the elements found were: C, 69.2%; H, 10.4%; N, 6.1%.

EXAMPLE 15

To a stirred mixture of cycloheptanone (73.2 g.) and ethanol (200 cc.), containing ammonium acetate (6.4 g.) and kept at or below 0°C was added 1-amino-3,3,5-trimethylcyclohexyl hydroperoxide (69.2 g.; 76% pure). After the solid had dissolved (5 hours) the solution was stored at 0°C overnight and the product worked up as in the previous Examples. There were obtained unreacted cycloheptanone, and dihydroisophorone, and fractions (57.5 g.) b.p. 124° – 130°/0.3 mm.Hg., peroxide equivalent 283, perchloric acid equivalent 278 shown by mass spectroscopy to contain the peroxide

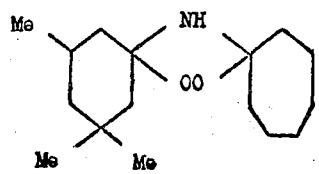

The elemental analysis gave C, 70.9%; H, 10.9%; N, 5.05% in agreement with formula (A).

EXAMPLE 16

To a stirred mixture of dihydroisophorone (28 g.) and ethanol (50 cc.), containing ammonium acetate (1.6 g.) kept at or below 0°C was added 1-amino-3,3,5-trimethylcyclohexyl hydroperoxide (17.3 g.; pure). The mixture was stored at 0°C for 4 days and then worked up as in the preceding Examples to give dihydroisophorone and a fraction (12.0 g.) b.p. 126° – 128° at 0.4 mm.Hg; peroxide equivalent 322. The elemental analysis gave C, 73.3%; H, 11.1%; N, 5.0%.

The product was identified as 1,1'-peroxy-3,3,5,3',-3',5'-hexamethyl-dicyclohexylamine

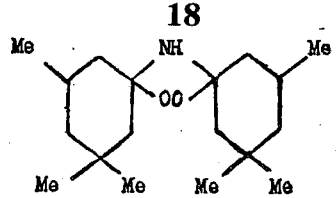

EXAMPLE 17

To a stirred mixture of cyclohexanone (19.6 g.) and ethanol (50 c.c.), kept at or below 0°C, was added 1-amino-3,3,5-trimethylcyclohexyl hydroperoxide (17.3 g., 78% pure); solution was complete in ca. 10 min. To the solution was added conc. sulphuric acid (3 drops) and magnesium sulphate and the mixture was stored at 0°C for 3 days. The solid was filtered off, the filtrate washed with water, dried and distilled, to give cyclohexanone, dihydroisophorone and a fraction (11.5 g.), b.p. 90° – 100° at 0.02 mm.Hg., peroxide equivalent 179. By mass spectroscopy the product was shown to contain the unsymmetrical peroxide and the symmetrical peroxide 1,1'-peroxydicyclohexylamine in the ratio 1:9.

EXAMPLE 18

To a stirred solution of cyclohexanone (19.6 g.) in ethanol (50 cc), containing ammonium acetate (1.6 g.) and kept at or below 0°, was added 1-amino-3,3,5-trimethylcyclohexyl hydroperoxide (17.3 g.; 78% pure). The solid dissolved in 5 – 10 min., then to the solution was added magnesium sulphate and the mixture stored at 0° overnight. Working up as in the previous Examples led to isolation of a peroxide fraction (13.1 g.) b.p. 98° – 104°/0.3 mm., with ratio of unsymmetrical to symmetrical peroxides of 1:9:8.

EXAMPLE 19

The reaction of Example 14 was repeated with the stirring carried out at –30°C, and overnight storage at –10°C. There was obtained peroxide (10.5 g.) having a ratio of unsymmetrical to symmetrical peroxide of 1:8.

EXAMPLE 20

To a stirred solution of cyclohexanone (19.6 g.) in dioxan (30 c.c.) kept at or below 0°, was added 1-amino-3,3,5-trimethylcyclohexanone (17.3 g.; 78% pure). After the solid had dissolved magnesium sulphate was added and the solution stored overnight at 0°C. Working up as in the previous Examples gave peroxide (4.5 g.) with a ratio of unsymmetrical to symmetrical compounds 1:12:1.

EXAMPLE 21

The process of Example 16 was repeated, but replacing the dioxan by dimethylformamide. There was obtained peroxide (10.5 g.) with a ratio of unsymmetrical to symmetrical peroxide of 1:8:6.

EXAMPLE 22

2-Methylcyclohexanone (51 g.), methanol (60 cc)., 0.880 ammonia (35 c.c.), 30% hydrogen peroxide (35 cc.) and EDTA (0.5 g.) were mixed together at room temperature and the solution saturated with gaseous ammonia. After standing together for one week, the product was extracted with ether, the extract dried with magnesium sulphate, the solvent evaporated, 2-methylcyclohexanone (21.3 g.) removed at 0.3 mm., and the residue treated with petrol. Some petrol-insoluble material, m.p. 77° – 79°, was separated, and petrol-soluble portion evaporated and residue distilled to give the required peroxide (7.9 g.), b.p. 107°/0.4 mm., and residue (0.6 g.). Redistillation of the peroxide gave material (b.p. 97° – 100°/0.7 mm.) having an active oxygen equivalent of 247, and a perchloric acid equivalent of 244. Elemental analysis gave C, 70.4%; H, 10.3%; N, 8.4%. The structure of the peroxide was confirmed by I.R. and N.M.R. spectroscopy as 1,1'-peroxy-2,2'-dimethyl-dicyclohexylamine

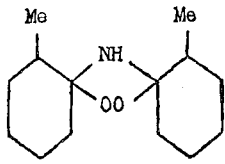

EXAMPLE 23

3-Methylcyclohexanone (50 g.), methanol (60 cc.), 0.880 ammonia (35 cc.), 30% hydrogen peroxide (35 cc.) and EDTA (0.5 g.) were mixed together at room temperature and saturated with gaseous ammonia. After standing for one week the product was extracted with ether. Distillation of the extract yielded 3-methylcyclohexanone and a product (27.1 g.), b.p. 105°/0.2 mm., and a residue (1.0 g.). The product was identified as 1,1'-peroxy-3,3'-dimethyl-dicyclohexylamine

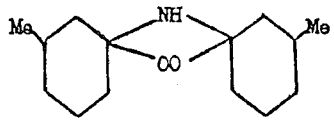

The peroxide equivalent was 235 and the perchloric acid equivalent was 256. The structure was confirmed by I.R. and N.M.R. spectroscopy.

EXAMPLE 24

4-Methylcyclohexanone (50 g.), methanol (120 cc.), 0.880 ammonia (135 cc.), 30% hydrogen peroxide (35 cc.), and EDTA (0.5 g.) were mixed at room temperature and the solution saturated with gaseous ammonia. The mixture was stored for one week during which time a solid product had separated. The product was extracted with light petrol (b.p. 40° – 60°) to give some insoluble material (6.8 g.), m.p. 79° – 80° (dec.), the 1-amino-4-methylcyclohexyl hydroperoxide; peroxide equivalent (active oxygen), 147.5; perchloric acid equivalent 165. The petrol-soluble material was obtained as solid (26.4 g.) m.p. 119° – 121°; active oxygen equivalent 224; perchloric acid equivalent, 235. The elemental analysis gave C, 70.1%; H, 10.5%; N, 6.0%. The I.R. and N.M.R. spectra were in agreement with this product being the desired 4,4'-dimethyl-1,1'-peroxy-dicyclohexylamine. The non-crystalline material (9.0 g.) contained 4-methyl-cyclohexanone together with further peroxide.

EXAMPLE 25

Dihydroisophorone (128 g.), 0.880 ammonia (240 cc.), 30% hydrogen peroxide (120 cc.), and EDTA (sodium salt) (2 g.) were mixed and methanol (450 cc.) added in sufficient quantity to give a homogeneous solution. The mixture was stirred at ca. 0° in a stream of ammonia and after a short time solid began to appear. When the solution became thick with solid it was filtered and the filtrate retreated with ammonia to yield further solid.

Distillation of the mother liquors from the reaction product from which the solid had been separated, yielded a small amount of the symmetrical peroxide 1,1'-peroxy-3,3,5,3',3',5'-hexamethyl dicyclohexylamine

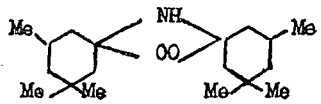

b.p. 115°C at 0.2 mm Hg. Elemental analysis gave C, 73.3%; H, 11.1%; N, 5.0%. The structure was confirmed by I.R. and mass spectrometry.

EXAMPLE 26

Cyclopentanone (77.5 g.), 0.880 ammonia (50 cc.), water (20 cc.), methanol (45 cc.), E.D.T.A. (sodium salt) (1.0 g.) and ammonia acetate (8.0 g.) were stirred together, and 30% hydrogen peroxide (70 cc.) added with cooling. After storing the mixture for two days at 0° the solution was extracted with ether. The ether extract, on distillation, yielded a low-boiling fraction (56 g.) b.p. 71°/0.1 mm. This product had a peroxide equivalent of 172, and perchloric acid equivalent of 195. Elemental analysis gave C, 4.7%; H, 8.9%; N, 7.6%. It solidified on storage and, when crystallised from cold petrol, had m.p. 22° – 23°C. This product was identified as 1,1'-peroxy-dicyclopentylamine.

EXAMPLE 27

Cycloheptanone (50 g.), methanol (60 cc.), 0.880 ammonia (35 cc.), 30% hydrogen peroxide (35 cc.) and E.D.T.A. (0.5 g.) were mixed at room temperature, saturated with gaseous ammonia and stored for one week. Extraction with ether, followed by distillation of the extract yielded cycloheptanone (44 g.), and a product (5.5 g.), b.p. 120° – 130°/0.8 mm., which had peroxide equivalent 331 and perchloric equivalent 306. This was identified as

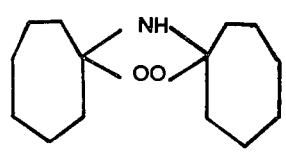

1,1'-peroxy-dicycloheptylamine and a residue (1.6 g.).

EXAMPLE 28

Cyclohexanone (90 g.) ammonia (50 cc.), water (20 cc.), methanol (45 cc.) and E.D.T.A. (1 g.) were stirred together and 30% hydrogen peroxide (70 cc.) gradually added with the reaction temperature kept at −35°. The mixture was stored at room temperature overnight, the product extract with ether, and the extract evaporated and the residue distilled to give cyclohexanone (22 g.) and a product which was identified as 1,1'-peroxy-dicyclohexylamine (64.4 g.), and leave a residue (2.0 g.). The peroxide distils at 94° – 97°/0.4 mm., 138° – 140°/12 mm, and has a melting point of 40° – 41.5°.

EXAMPLE 29

The same conditions were used as in Example 28 except that after the period of storage the bottom oily layer was separated, dissolved in ethanol, and the ethanolic solution added, with stirring, to water (2 liters). The 1,1'-peroxy-dicyclohexylamine separated as solid and filtered off. The yield of slightly wet product was 82 g., redistillation giving 72.6 g. of pure peroxide.

EXAMPLE 30

Cyclohexanone (90 g.), 0.880 ammonia (32 cc.), water (20 cc.), methanol (45 cc.) and E.D.T.A. (0.2 g.) were stirred together and 30% hydrogen peroxide (70 cc.) gradually added with the reaction temperature kept at −35°. The mixture was stored at room temperature overnight, the oily layer separated, diluted with an equal volume of methanol and the methanolic solution added, with stirring, to cold water (2 liters). Solid was filtered off and on distillation gave the peroxide 1,1'-peroxy-dicyclohexylamine (71.5 g.).

EXAMPLE 31

Cyclohexanone (90 g.), 0.880 ammonia (50 cc.), water (20 cc.), methanol (45 cc.) and E.D.T.A. (1.0 g.) were stirred together, and 30% hydrogen peroxide (70 cc.), added, with the reaction temperature kept at −35°. The temperature was kept at 35° for 4 hours and gaseous ammonia slowly passed into the solution. The mixture was stored overnight at room temperature; the peroxide crystallised out from the solution on addition of water and was filtered off. Distillation gave cyclohexanone (3.5 g.) and 1,1'-peroxy-dicyclohexylamine (77.8 g.). The aqueous phase was extracted with ether and provided cyclohexanone (4.8 g.) and no peroxide.

EXAMPLE 32

1,1'-Dihydroxydicyclohexyl peroxide (26.5 g.) 0.880 ammonia (12.5 cc.), water (35 cc.), methanol (12 cc.) and E.D.T.A. (0.2 g.) were stirred together until the solid peroxide had dissolved and the mixture left at room temperature overnight. The product was extracted with ether and the ethered extract on distillation, gave cyclohexanone (<1 g.) and 1,1'-peroxydicyclohexylamine (17.6 g.).

The 1,1'-peroxydicyclohexylamine may also be made by reacting the autoxidate of cyclohexanol i.e. the product of oxidation of cyclohexanol with molecular oxygen, with ammonia.

EXAMPLE 33

A mixture of dihydroisophorone (44.9 g.; 0.31 mole), 0.880 ammonia (110 cc.), ethanol (150 cc.), and E.D.T.A. (sodium salt) (0.5 g.) was cooled and ca. 30% hydrogen peroxide (40 cc.; 0.375 mole) added. The stirred mixture was kept at below 0°C and ammonia gas passed in. After 6 hours the solid produced was filtered off and the filtrate cooled and retreated with ammonia. Two further crops of solid were obtained. The solid had perchloric acid equivalent of 181 and peroxide equivalent of 164 and elemental analysis gave C, 65.2%; H, 10.9%; N, 7.8%, was washed with water, cold alcohol, then petrol, and dried in vacuo: yield, 33.4 g. (0.19 mole). The product was identified as 1-amino-3,3',5'-trimethylcyclohexyl hydroperoxide.

The filtrate and washings were found to contain 0.15 mole unreacted hydrogen peroxide and 0.115 mole dihydroisophorone.

EXAMPLE 34

Dihydroisophrone (44.9 g.; 0.31 mole), 0.880 ammonia (60 cc.), methanol (150 cc.), and E.D.T.A. (sodium salt) (0.5 g.) were mixed and cooled; ca. 30% hydrogen peroxide (40 cc.; 0.375 mole) was added, and the stirred, cooled mixture treated with ammonia as above.

There were obtained 1-amino-3,3',5'-trimethylcyclohexyl hydroperoxide (48.9 g.; 0.275 mole), dihydroisophorone (4.3 g.; 0.31 mole), and there was present in the filtrate and washings 0.1 mole unreacted hydrogen peroxide.

EXAMPLE 35

4-Methylcyclohexanone (50 g.), methanol (120 cc.), 0.880 ammonia (135 cc.), 30% hydrogen peroxide (35 cc.) and E.D.T.A. (0.5 g.) were mixed at room temperature (ca. 20°C) and the solution saturated with gaseous ammonia. The mixture was stored for one week, during which time a solid product separated. The product was extracted with light petrol (b.p. 40° – 60°C). Insoluble material (6.8 g.) remained after the extraction. This material had m.p. 79° – 80° (dec.) peroxide equivalent 147.5 and perchloric acid equivalent 165 and was identified as 1-amino-4-methylcyclohexyl hydroperoxide.

EXAMPLE 36

Cyclododecanone (60.6 g.) was mixed with ethanol (450 cc.), 86% hydrogen peroxide (13.4 g.), 0.880 ammonia solution (20 cc.) ammonia acetate (3 g.) and E.D.T.A. (sodium salt; 1 g.), the solution saturated with gaseous ammonia and stored at ca. 0° for 3 days. The solid aminohydroperoxide (57.6 g) was filtered off. A portion recrystallised from benzene had m.p. 72° – 73°, a peroxide equivalent of 210, and perchloric acid equivalent of 215 (calc. 215). The I.R. and N.M.R. spectra were in agreement with the proposed structure, and it had an elementary analysis of C, 66.3; H, 11.5; N, 6.1%. Calc. for $C_{12}H_{25}NO_2$: C, 66.9; H, 11.6; N, 6.5%.

EXAMPLE 37

30% Hydrogen peroxide (70 cc.) was added rapidly to a stirred solution of cyclohexanone (49 h.) and E.D.T.A. (sodium salt) (0.5 g.) in methanol (30 cc.) and 0.880 ammonia (55 cc.). The temperature rose to ca. 30°, but rapid cooling reduced this to 0° – 15°; storage for 1 hour at <0° ceased crystallisation. The product was filtered off, washed well with ice-cold water, then petrol, and dried on a porous plate; this product (57 g.), had m.p. 57° – 58° (rapid heating), 47° (slow heating) (With decomposition) and had a peroxide equivalent of 140 and perchloric acid equivalent of 135 (calc 131). Found: C, 55.1; H, 9.85; N, 10.9; calc for $C_6H_{13}NO_2$; C, 55.0; H, 9.95; N, 10.7%.

EXAMPLE 38

1-Aminocyclohexyl hydroperoxide (13.1 g.), cyclohexanone (9.8 g.) methanol (25 cc.) and ammonia acetate (1.0 g.) were mixed and stored at 0° overnight. Next day the product was diluted with water, extracted with ether and the ethereal extract distilled to give unreacted cyclohexanone and 1,1'-peroxydicyclohexylamine (12.5 g.), which recrystallised from petrol had m.p. 39.5° – 40.5°, undepressed on admixture with authentic peroxide.

EXAMPLE 39

1-Aminocyclohexyl hydroperoxide (13.1 g.), dihydroisophorone (14 g.), methanol (25 cc.) and ammonia acetate (1.0 g.) were mixed, stored at 0°C overnight and worked up as in the previous Example. Distillation gave cyclohexanone and dihydroisophorone (9.0 g.), an intermediate fraction (3.2 g.), b.p. below 100°C/0.7 mm., Hg., a fraction (8.1 g.), b.p. 110° – 114°10.7 mm. of 3,3,5'-trimethyl-1,1'-peroxy-dicyclohexylamine (peroxide equivalent, 234; perchloric acid equivalent, 245; and residue (1.5 g.).

EXAMPLE 40

1-Aminocyclohexyl hydroperoxide (13.1 g.), butyraldehyde (7.2 g.), methanol (25 cc.) and ammonia acetate (1.0 g.) were mixed and stored at 0°C overnight. Working up as in Example 39 gave cyclohexanone and butyraldehyde, and a product (8.4 g.), b.p. 89°/0.3 mm. (peroxide equivalent, 204; pechloric acid equivalent, 206; which was identified as

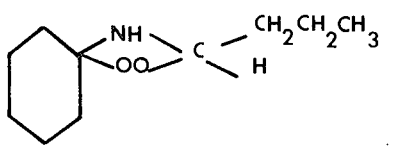

The number of carbon atoms in each of the radicals X and X' which form part of the rings shown in Formula (IV) may for example vary from 4 to 11, i.e. there may be from 5 to 12 carbon atoms in each ring. In particular 4 to 6 of the carbon atoms in each of X and X' may form part of the rings. Examples of such compounds are a.

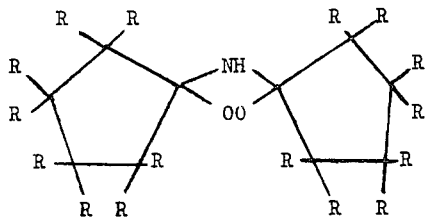

and b.

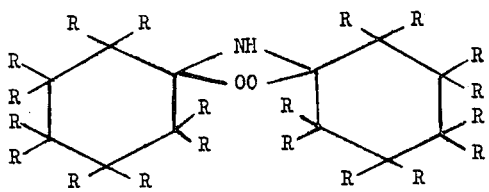

and c.

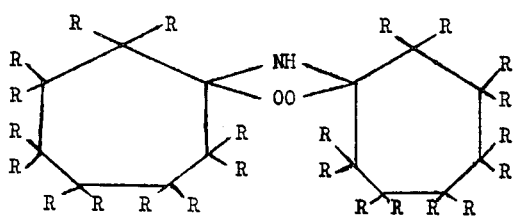

where R is alkyl or hydrogen.

The preferred compounds are those in which R is hydrogen or lower alkyl, e.g. having 1 to 10 carbon atoms in the chain, in particular those having from 1 to 5 carbon atoms in the chain e.g. methyl, ethyl, propyl.

Specific examples of compounds which can be used in the process of the present invention are:

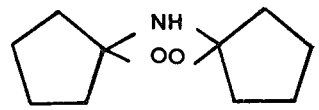

1,1'-peroxydicyclopentylamine.

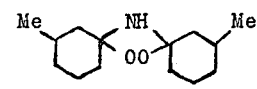

3,3'-dimethyl-1,1'-peroxydicyclohexylamine.

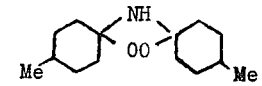

4,4'-dimethyl-1,1'-peroxydicyclohexylamine

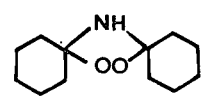

1,1'-peroxydicyclohexylamine

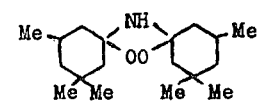

3,3,3',3',5,5'-hexamethyl-1,1'-peroxydicyclohexylamine

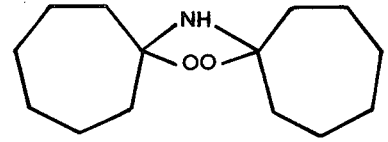

1,1'-peroxydicycloheptylamine.

The relationship between the structure of the lactam produced according to the present invention and the structure of the compound (IV) from which it is produced will now be discussed. In this discussion reference will be made to the radicals X and X', as it is convenient to do so to show which lactams are produced. It is not intended to imply, however, that the radical X necessarily exists as a free radical in the reaction mixture or to put forward any theory of the mechanism of the reaction.

The nature of the lactam produced will depend upon the nature of the rings, of which the radicals X, X' form part, in the compound of formula (IV). The lactam will have the same number of carbon atoms in the lactam ring as in the carbocyclic ring from which it is derived, and any substitutents on the carbon atoms of the lactam ring will correspond to the substituents on the ring from which it is derived. The radical X remains intact and two lactam isomers may result as the conversion of the compound (IV) to the lactam involves a rearrangement in which the imino group may be introduced on either side of the carbon atom originally linked to the peroxy group. The lactams thus produced are

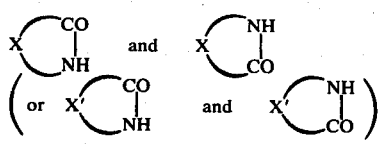

Thus, 3,3'-dimethyl-1,1'-peroxy-dicyclohexylamine

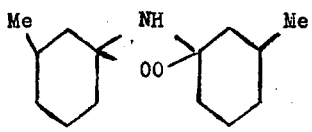

(which may be produced, probably as a mixture of stereoisomers, by reaction of 3-methylcyclohexanone with hydrogen peroxide and ammonia) can be decomposed to give 3-methyl caprolactam and 5-methyl caprolactam.

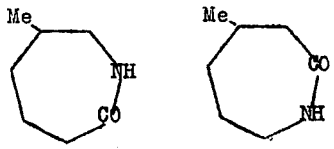

5-methylcaprolactam    3-methylcaprolactam

When the compound of formula (IV) is unsubstituted (or substituted symmetrically relative to the linkage to the 1,2,4-dioxazolidine ring) the same lactam may be produced no matter to which valency of radical X the imono group bonds, and in that case only one isomer is produced. Thus the lactam yielded by the decomposition of 1,1'-peroxydicyclohexylamine is solely caprolactam, and that from the decomposition of 4,4'-dimethyl-1,1,'-peroxy dicyclohexyl amine is solely 4-methyl caprolactam.

If X and X' are different and unsubstituted (or symmetrically substituted) only two lactams could be formed, e.g.

If X is unsubstituted (or symmetrically substituted) and X' is unsymmetrically substituted three lactams are possible, e.g.

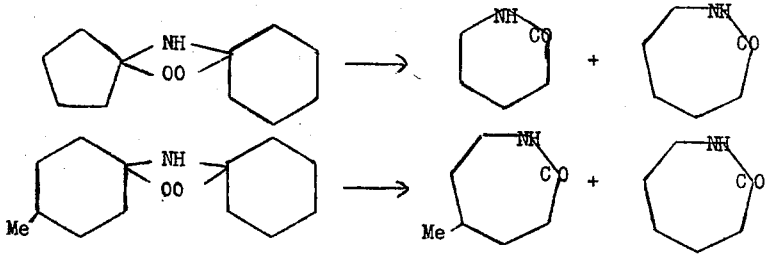

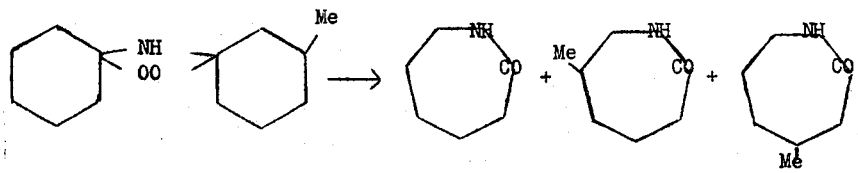

If X and X' are both unsymmetrically substituted then four lactams are possible, but of course it is possible that particular isomers might be favored by the reaction conditions chosen.

The peroxyamine fed to the thermal decomposition reaction may be in the form of the pure compound separated from the reaction mixture in which the peroxyamine is formed. Peroxyamine-rich products which can be readily separated from the reaction in which peroxyamine is produced may be used however without further purification. Thus in the production of peroxyamines by reaction of cyclic ketones, hydrogen peroxide and ammonia, the peroxyamine often separates as an oil layer, containing also unchanged ketone, from the aqueous reaction medium. This oil layer can be fed to the thermal decomposition reaction without isolation of the peroxyamine.

The compound (IV) may be heated in the liquid phase in any convenient manner. Thus the molten compound (IV) may be heated, or alternatively the compound (IV) may be heated dissolved in a solvent. Where the compound (IV) is dissolved in a solvent the concentration of the compound of formula (IV) in the solution may vary over a wide range. The quantity of solvent used may be only that sufficient to give a liquid product. Thus the crude product from the production of compounds of formula (IV) is often liquid even when the pure compound (IV) is solid, because the crude product contains cyclic ketone, up to about 10% by weight of the total crude product. The quantity of solvent present can of course be much larger than this and examples of concentrations of (IV) which can be used are those in the range 5% to 75% by weight/weight.

The maximum concentration that can be used will of course depend upon the solubility of compound (IV) in the solvent.

Examples of solvents which may be used as aromatic amines such as pyridine and β-picoline, and those solvents commonly known as polar or ionizing solvents such as lower aliphatic alcohols, amines, amides, sulphoxides, and nitriles. Specific examples of such solvents include methanol, ethanol, ethylene diamine, dimethyl formamide, dimethyl sulphoxide, and acetonitrile. Other solvents include ketones such as cyclohexanone and n-amyl methyl ketone, and lactams, e.g. the lactam product itself.

The decomposition of the compound (IV) to lactams may be carried out in the presence of a catalyst. Thus both the molten compound (IV) or a solution of (IV) in a solvent may be heated with a catalyst.

Examples of catalysts which may be used in the liquid phase reaction are alkoxides, aryloxides, and mixtures of akali metal hydroxides with alkanols or hydroxy-substituted aryl compounds.

The term "aryloxides" as used in this specification means compounds formed by the replacement of hydrogen by a metal in a hydroxy group linked directly to an aromatic nucleus. An example of a suitable aryloxide is sodium phenoxide

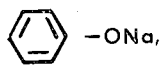

but other phenoxides with substituents other than hydroxy groups may be used. The preferred aryloxides are those derived from the benzene nucleus. The term "hydroxyaryl compounds" as used in this specification means the compounds in which the hydroxy group is linked directly to an aromatic nucleus. Examples of suitable hydroxyaryl compounds are those from which the "aryloxides" referred to above may be derived.

The alkali metal alkoxide, aryloxide or hydroxide may be an alkoxide, aryloxide or hydroxide of any of the alkali metals, e.g. lithium, sodium or potassium. Sodium is particularly preferred.

Examples of suitable alkoxides are the lower alkoxides, e.g. ethoxide or methoxide, methoxides being preferred. Butoxides, in particular n-butoxides, are suitable and the use of n-butoxides is particularly advantageous, as they can be isolated from the reaction of n-butanol and alkali metal hydroxides. It is not necessary however to isolate the alkoxide which may be formed in situ in the reaction mixture. If alkali metal hydroxides are combined with alkanols and hydroxyaryl compounds with elimination of water, alkoxides or aryloxides will be produced, and the mixtures of alkali metal hydroxides with alkanols or hydroxyaryl compounds will often contain alkoxides or aryloxides in equilibrium with the hydroxide. The presence of the water produced by the reaction of the alkanol or hydroxy aryl compound with the alkali metal hydroxide may however give rise to side-reactions which do not take place when the reaction is carried out using alkoxides or aryloxides prepared by methods which do not involve the production of water. Where mixtures of alkali metal hydroxide and alkanols are used examples of suitable alkanols are the lower alkanols, e.g. methanol, ethanol and butanol. The quantity of alkanol used is preferably in excess of 1 mole of alkanol per mole of alkali metal hydroxide.

Where a mixture of alkali metal alkoxide and alkanol is used, the alkanol will also act as a solvent. The compound (IV) and the mixture of hydroxide and alkanol are preferably brought together in the absence of added water e.g. in solution in a substantially anhydrous alkanol. It may be adantageous to carry out the reaction in the presence of a drying agent e.g. CaO, $MgSO_4$, $Na_2SO_4$.

Where the compound (IV) is heated with an alkali metal alkoxide, aryloxide, or a mixture of alkali metal hydroxide and an alkanol or hydroxy-aryl compound in solution examples of solvents which may be used are aromatic hydrocarbons, e.g. benzene, phenols and/or alkanols e.g. ethanol or methanol. Solvents of high dielectric constant lead to high rates of reaction although the yield of lactam may be reduced. The preferred solvents are alkanols and when an alkoxide is used, the alkanol is preferably the alkanol corresponding to the alkoxide, thus when using a methoxide the reactants are preferably dissolved in methanol and when using an ethoxide the reactants are preferably dissolved in ethanol. However, when using higher alkoxides and aryloxides the lower alkanols are the most suitable solvents. Thus, when using n-butoxide, or a phenoxide, the most satisfactory results are obtained if the reaction with 1,1'-peroxydicyclohexylamine or other peroxyamines is carried out in methanol.

Examples of suitable ratios of the number of moles of the alkali metal compound (whether alkoxide, aryloxide or hydroxide) to the number of moles of peroxyamine (IV) are 0.2 to 2. When the reaction is being carried out in solution the concentration of the reactants may vary within moderately wide limits.

The optimum temperature for decomposing compound (IV) to lactam will depend upon the compound (IV) and the reaction conditions, and upon the nature of any catalyst and/or solvent used. Temperatures between 40°C and 200°C e.g. 50° – 200°C are generally best. Where the compound (IV) molten, or in solution, is heated without a catalyst optimum temperatures will generally be obtained at temperatures in the range 60°C – 120°C. Where the compound (IV), molten in solution is heated with a catalyst good results may often be obtained at temperatures which are lower than those which are the best when no catalyst is present. Thus where compound (IV) is heated with alkali metal alkoxide or aryloxide without a solvent the best results are obtained with temperatures in the range 30° to 150°C, e.g. 40°–150°C. Where solutions of compound (IV) are heated with alkali metal alkoxide, aryloxide, or mixtures of alkali metal hydroxide with alkanols or hydroxy-aryl compounds examples of temperatures which may be used are those in the range 40°C–160°C in particular 50°C to 100°C.

The duration of the reaction will depend upon the reaction conditions. Examples of suitable times are those in the range 0.1 to 10 hours. The reaction is complete when no more peroxide can be detected in the reaction mixture. The presence of unreacted peroxide may be detected by reacting the reaction mixture with an excess quantity of potassium iodide in acetic acid. Any peroxide present liberates iodine which can be estimated by titration with sodium thiosulphate.

The reaction may be carried out at sub-atmospheric and super-atmospheric pressure as well as at atmospheric pressure. The reaction may be carried out under conditions of temperature and pressure such that any solvent is under reflux so helping to maintain a constant reaction temperature.

The lactam may be recovered from the reaction mixture by any convenient method. Thus it may be possible to distil the lactam from the reaction mixture, provided there is nothing present e.g. a solvent which has a boiling point very close to that of the lactam. In an alternative method which may be applied to reaction mixtures containing alkali metal hydroxides, alkoxides, or aryloxides the reaction mixture is diluted with water, followed by extraction of the mixture with a liquid which is immiscible with water and is a solvent for the lactam produced. Examples of suitable liquids are aromatic compounds, e.g. benzene, xylene, and chlorinated hydrocarbons especially the chlorinated lower aliphatic hydrocarbons, e.g. methylene chloride, chloroform, dichloroethane. Ethers, e.g. diethyl ether, may also be used. Acid may optionally be added to the reaction mixture after addition of water. The quantity of acid is suitable such as to make the reaction mixture just acid to Congo red indicator. If desired, the solvent used to dissolve the reactants may be removed before the dilution with water. The liquid used to extract the lactam is then distilled from the extract to leave the lactam and cyclic ketone which may be separated e.g. by distillation.

The invention will now be illustrated by the following examples in which all temperatures are in celsius degrees and all pressures in millimeters of mercury.

EXAMPLE 41

Sodium (2 g.) was dissolved in methanol (30 c.c.) and 1,1'-peroxydicyclohexylamine (10 g.), dissolved in methanol (10 c.c.) added. The mixture was heated under reflux for 1½ hrs when no peroxide remained. Water (ca. 30 c.c.) was added to the reaction mixture and the solution made just acid to Congo red with hydrochloric acid; extraction with chloroform followed by evaporation of the solvent and distillation at 15 mm. gave cyclohexanone (4.7 g.) and a caprolactam fraction (4.2 g.) containing 93% by weight of caprolactam (by infra-red spectroscopy).

EXAMPLE 42

The same procedure was used as in Example 1 but at the end of the reflux period the bulk of the methanol was evaporated at 15 mm., the residue diluted with water, neutralised with acid and extracted with chloroform. Distillation gave cyclohexanone (4.1 g.) and a caprolactam fraction (4.5 g.), 87% pure by infra-red spectroscopy.

EXAMPLE 43

The same procedure was used as in Example 1 but replacing methanol by ethanol. Heating time one-half hour. Distillation gave cyclohexanone (2.3 g.), a caprolactam fraction (3.7 g.), a higher boiling fraction (2.4 g.) and residue (0.7 g.). The caprolactam fraction contained 70% by weight of caprolactam by infra-red spectroscopy.

EXAMPLE 44

Sodium (1.2 g.) was dissolved in ethanol (50 c.c) and 1,1'-peroxydicyclohexylamine (10 g.) in ethanol (40 c.c) added. The resulting solution was refluxed for 4 hours, the bulk of the ethanol removed on the water pump and the residue treated as in Example 1. There were obtained cyclohexanone (2.5 g.)., caprolactam fraction (4.0 g.) containing 76% by weight of caprolactam, a higher-boiling fraction (1.2 g.) containing 10–15% caprolactam, and a residue (0.5 g.).

EXAMPLE 45

Potassium (3.4 g.) dissolved in methanol (30 c.c.) was treated with 1,1'-peroxydicyclohexylamine (10 g.) in methanol (10 c.c.) and the mixture refluxed for 2 hours. The reaction mixture was treated as in Example 1 and gave cyclohexanone (3.6 g.), a caprolactam fraction (3.8 g.) containing 83% caprolactam by weight, and a residue (0.5 g.).

EXAMPLE 46

Lithium (0.8 g) dissolved in methanol (40 c.c.) and 1,1'-peroxydicyclohexylamine (10 g.) in methanol (10 c.c.) were mixed and refluxed for 10½ hours. The reaction mixture was treated as in Example 1 and gave cyclohexanone (3.8 g.), a caprolactam fraction, (2.7 g.), containing 5% caprolactam by weight, a higher-boiling fraction (1.0 g.) containing 30% caprolactam by weight, and residue (0.5 g.).

EXAMPLE 47

Sodium (2 g.) was dissolved in methanol (25 c.c.) and 1,1'-peroxydicyclohexylamine (10 g.) added, the mixture was refluxed for 1 hour. The reaction product was then diluted with water, and then extracted with chloroform without acidification to give cyclohexanone (2.9 g.), a caprolactam fraction (4.8 g.), containing 65% caprolactam by weight, a higher-boiling fraction (0.3 g.), containing 37% caprolactam by weight and a residue (0.2 g.).

EXAMPLE 48

Sodium hydroxide (3.5 g.) was dissolved in methanol (30 c.c.) and 1,1'-peroxydicyclohexylamine (10 g.) dissolved in methanol (10 c.c.) was added and the mixture heated to reflux for 2½ hours. After heating the solution was diluted with water and extracted with chloroform. Distillation gave a cyclohexanone fraction (4.0 g.), a caprolactam fraction (4.4g.) containing 75% lactam by I.R.), and residue (0.1 g.).

EXAMPLE 49

The same reactants heated to reflux were used as in Example 8 with the addition of magnesium sulphate monohydrate (1.5 g.) to the refluxing solution. Heating was continued for 5¼ hours. Treatment of the reaction mixture as in Example 8 gave a cyclohexanone fraction (2.8 g.), a caprolactam fraction (4.1 g. containing 81% lactam by I.R.), and residue (0.2 g). Further caprolactam (0.2 g.) was obtained by acidification of the aqueous phase followed by extraction with chloroform.

EXAMPLE 50

The same reactants were refluxed together as in Example 8 with the addition of calcium oxide (2 g.) to the refluxing solution. Heating was continued for 2¼ hours. Treatment of the reaction mixture as in Example 8 gave a cyclohexanone fraction (3.7 g.), a caprolactam fraction (4.2 g. containing 85% lactam by I.R.), and residue (0.2 g.).

EXAMPLE 51

The same reactants were refluxed together as in Example 8 with the addition of water (2 c.c.) to the refluxing solution. Heating was continued for 3 hours. Treatment of the reaction mixture as in Example 8 gave a cyclohexanone fraction (3.3. g.), a caprolactam fraction (4.5 g. containing 65% lactam by I.R.) and residue (0.2 g.).

EXAMPLE 52

Potassium hydroxide (4.9 g.), methanol (40 c.c.) and 1,1'-peroxydicycohexylamine (10 g.) were heated together under reflux for 2¾ hours. Treatment of the reaction mixture as in Example 8 gave a cyclohexanone fraction (1.9 g.), a caprolactam fraction (4.4 g. containing 80% by lactam by I.R.), and a higher-boiling fraction (0.4 g. containing 55% lactam I.R.).

EXAMPLE 53

Sodium hydroxide (3.5 g.), ethanol (70 c.c.) and 1,1'-peroxydicyclohexylamine (10 g.) were heated under reflux for 2¾ hours. Treatment of the reaction

31 mixture as in Example 8 gave a low-boiling fraction (1.7 g.), a caprolacta fraction (4.2 g. containing 75% lactam by I.R.), a higher boiling fraction (0.9 g.), and residue (0.4 g.).

EXAMPLE 54

Sodium hydroxide (3.5 g.), ethanol (40 c.c), and 1,1'-peroxydicyclohexylamine (10 g.) were heated under reflux for 1¾ hours. Treatment of the reaction mixture as in Example 8 gave a low-boiling fraction (3.2 g., largely cyclohexanol by I.R.), a caprolactam fraction (3.9 g. containing 60% lactam by I.R.), a higher-boiling fraction (1.2 g.) and residue (0.5 g.).

EXAMPLE 55

Sodium n-butoxide (from 2 g. of sodium) was dissolved in methanol (25 c.c.) and 1,1'-peroxydicyclohexylamine (10 g.) in methanol (10 c.c.) added. The solution was heated under reflux for 1½ hours; the methanol was evaporated off under reduced pressure, water added to the residue and the solution extracted with chloroform. Distillation gave a fraction containing n-butanol and cyclohexanone (2.2. g. of the ketone by estimation with hydroxylamine hydrochloride), a caprolactam fraction (5.1 g. containing 87% lactam by I.R.) and a residue (0.3 g.).

EXAMPLE 56

Sodium phenoxide (11.0 g.) in methanol (30 c.c) was mixed with 1,1'-peroxydicyclohexylamine (10 g.) in methanol (10 c.c.) and heated under refluxed for 6¼ hours. The product was diluted with water, the solution extracted with chloroform and the extract distilled to give cyclohexanone (1.8 g), a caprolactam fraction (4.3 g. containing 70% lactam by I.R.) and residue (0.15 g.).

EXAMPLE 57

3,3'-Dimethyl-1,1'-peroxydicyclohexylamine (10 g.) derived from 3-methylcyclohexanone, hydrogen peroxide and ammonia, and probably a mixture of stereoisomers was added to a solution of sodium methoxide in methanol (2 g. sodium in 40 c.c. methanol) and the mixture heated under reflux for 2 hours; only a small amount of peroxide remained unreacted. The solution was cooled, diluted with water, neutralised with hydrochloric acid and extracted with chloroform. Distillation of the chloroform extract gave 3-methylcyclohexanone (4.7 g.), methylcaprolactam (4.1 g), b.p. 145°–150°/15 mm., and residue (0.5 g.). Examination of the methylcaprolactam fraction by N.M.R. spectroscopy showed it to be a mixture of 3- and 5-methyl-caprolactam; on storage this fraction crystallized and several recrystallisations yielded the 3-methylcaprolactam, m.p. 87°–100°.

EXAMPLE 58

4,4'-Dimethyl-1,1'-peroxydicyclohexylamine (5 g.) derived from the reaction of 4-methylcyclohexanone, hydrogen peroxide and ammonia) was added to a solution of sodium methoxide in methanol (1 g. of sodium in 20 c.c. methanol) and the mixture heated under reflux for 2 hours when very little peroxide remained unreacted. The product was worked up as in Example 17 to give, on distillation, 4-methylcyclohexanone (2.2 g.), 4-methyl-caprolactam (2.2 g.), b.p. 145°–150°/15 mm, and residue (0.3 g.). The structure of the lactam was confirmed by I.R. and N.M.R. spectra.

EXAMPLE 59

3,3,3',3',5,5'-Hexamethyl-1,1'-peroxydicyclohexylamine (75 g.) (derived from the reaction of dihydroisophorone, ammonia and hydrogen peroxide) probably a mixture of stereoisomers, was added to a solution of sodium methoxide in methanol (1.5 g. of sodium in 30 c.c. methanol) and the mixture heated under reflux for 2 hours when very little peroxide remained unreacted. The product was worked up as in Example 17 to give, on distillation, dihydroisophorone (4.1 g.) trimethyl caprolactam (3.1 g.), and residue (0.1 g.). The structure of the lactam was confirmed by I.R. and N.M.R. spectra; the N.M.R. spectrum showed that both

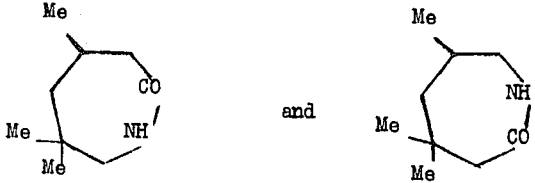

were present, the latter being the major component.

EXAMPLE 60

1,1'-Peroxydicyclopentylamine (10 g.) derived from the reaction of cyclopentanone, ammonia and hydrogen peroxide, was heated to reflux with sodium (2 g.) in methanol (40 c.c.). After reflux for one-fourth hour the product was worked up as in Example 17 and valerolactam obtained.

Valerolactam was also obtained when the experiment was repeated using 5 g. of the peroxide, 0.65 g. of sodium and a reflux time of 2½ hours.

EXAMPLE 61

1,1'-Peroxydicyclohexylamine (8 g.) in pyridine (50 g.) containing Triton B (Triton B is benzyl trimethylammonium hydroxide) (0.1 c.c. of a 40% aqueous solution) was heated under reflux at atmospheric pressure for 12½ hours. Distillation of the mixture, which still contained 20% unreacted peroxide gave, in addition to pyridine and cyclohexanone, a fraction (2.0 g.), b.p. 125°–155°/15 mm., containing 40% caprolactam together with the peroxide and a fraction (2.5 g.), b.p. 155°–270°/15 mm., containing a small amount of caprolactam but consisting mainly of the $C_{12}$ acid-amide, 11-carbamoylundecanoic acid.

EXAMPLE 62

1,1'-Peroxydicyclohexylamine (8 g.) in β-picoline (10 g.) was added during 1¼ hour, to boiling β-picoline (10 g.) (bath temperature 175°–180°C); refluxing at atmospheric pressure was continued for a further 1¼ hours to decompose the remainder of the peroxide. Distillation gave in addition to β-picoline and cyclohexanone, fractions (1.6 g.) consisting largely of caprolactam, and a fraction (2.2 g.), b.p. 250°–260°C at 15 mm.Hg., from which were isolated the $C_{12}$ diamide, 11-carbamoylundeconoamide m.p. 187°–190.5°, and the $C_{12}$ acid amide, 11-carbamoylundecanoic acid, m.p. 132°–134°C.

I claim:

1. The process for the production of lactams which comprises heating in the liquid phase a compound of formula

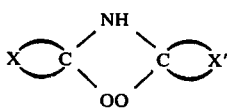

(IV)

wherein X and X' are divalent aliphatic moieties of 4 to 11 carbon atoms which may be the same or different, to a temperature in the range of from 40°C to 200°C to decompose it to a lactam.

2. The process according to claim 1 wherein the number of carbon atoms in each of X and X' which form part of the ring shown in formula (IV) is from 4 to 6 carbon atoms.

3. The process according to claim 2 wherein compound (IV) has the formula

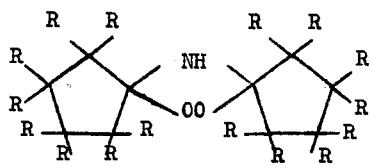

where R is alkyl or hydrogen.

4. The process according to claim 2 wherein (VI) has the formula

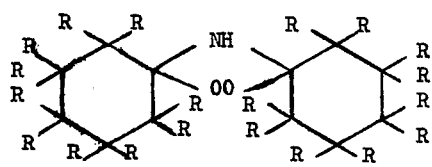

wherein R is alkyl or hydrogen.

5. The process according to claim 2 wherein the compound (IV) has the formula

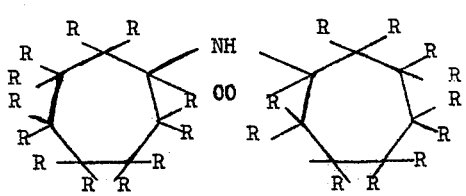

where R is alkyl or hydrogen.

6. The process according to claim 3 wherein compound (VI) is 1,1'-peroxydicyclopentylamine

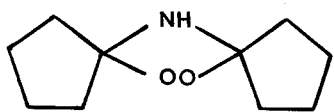

7. The process according to claim 4 wherein compound (IV) is 1,1'-peroxydicyclohexylamine

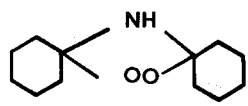

8. The process according to claim 4 wherein compound (IV) is 4,4'-dimethyl-1,1'-peroxydicyclohexylamine

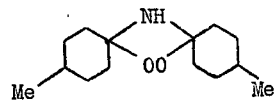

9. The process according to claim 4 wherein compound (IV) is 3,3'-dimethyl-1,1'-peroxydicyclohexylamine.

10. The process according to claim 1 wherein the molten compound (IV) is heated.

11. The process according to claim 1 wherein compound (IV), dissolved in a solvent, is heated.

12. The process according to claim 10 wherein compound (IV) is heated with a catalyst.

13. The process according to claim 1 wherein compound (IV) is heated with an alkoxide, aryloxide, or with a mixture of alkali metal hydroxide with alkanol or hydroxyaryl compound.

14. The process according to claim 1 wherein 1,1'-peroxydicyclohexylamine is heated with an alkali metal alkoxide.

15. The process according to claim 1 wherein 1,1'-peroxydicyclohexylamine is heated with a mixture of an alkali metal hydroxide and alkanol.

16. The process according to claim 1 wherein 1,1'-peroxydicyclohexylamine is heated with an aryloxide or a mixture of an alkali metal hydroxide and a hydroxyaryl compound.

17. The process according to claim 12 wherein compound (IV) is heated with the mixture of alkali metal hydroxide and alkanol in the absence of water.

18. The process according to claim 13 wherein compound (IV) is heated with a mixture of alkali metal hydroxide and methanol, ethanol or propanol.

19. The process according to claim 15 wherein 1,1'-peroxydicyclohexylamine is heated with a mixture of alkali metal hydroxide and methanol, ethanol and propanol.

20. The process according to claim 1 wherein compound (IV) dissolved in an aromatic hydrocarbon, a phenol or an alkanol, is heated with the alkali metal alkoxide, aryloxide, or mixture of alkali metal hydroxide and alkanol or hydroxyaryl compound.

21. The process according to claim 20 wherein compound (IV) is dissolved in methanol.

22. The process according to claim 13 wherein the alkali metal hydroxide, alkoxide or aryloxide, is a hydroxide, alkoxide or aryloxide of sodium or potassium.

23. The process according to claim 13 wherein the alkoxide is a methoxide or ethoxide.

24. The process according to claim 13 wherein the molar ratio of alkali metal hydroxide, alkoxide or aryloxide to compound (IV) is from 0.2 to 2.

25. The process according to claim 1 wherein compound (IV) is heated to a temperature in the range of from 50°C to 200°C.

26. The process according to claim 25 wherein the temperature is in the range of from 60°C to 120°C.

27. The process according to claim 11 wherein molten compound (IV) is heated with an alkali metal alkoxide or aryloxide to temperatures in the range of from 40°C to 150°C.

28. The process according to claim 13 wherein a solution of compound (IV) is heated to a temperature in the range of from 40°C to 160°C.

29. The process according to claim 28 wherein the temperature is in the range of from 50°C to 100°C.

* * * * *